US012564620B2

(12) United States Patent
Dixon

(10) Patent No.: US 12,564,620 B2
(45) Date of Patent: Mar. 3, 2026

(54) TREATMENT OF GULF WAR ILLNESS

(71) Applicant: VIRGINIA COMMONWEALTH UNIVERSITY, Richmond, VA (US)

(72) Inventor: Kirsty J. Dixon, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 319 days.

(21) Appl. No.: 17/945,993

(22) Filed: Sep. 15, 2022

(65) Prior Publication Data

US 2023/0372445 A1     Nov. 23, 2023

Related U.S. Application Data

(60) Provisional application No. 63/244,469, filed on Sep. 15, 2021.

(51) Int. Cl.
| | |
|---|---|
| *A61K 38/19* | (2006.01) |
| *A61K 47/10* | (2017.01) |
| *A61P 25/00* | (2006.01) |
| *C12N 5/0775* | (2010.01) |

(52) U.S. Cl.
CPC ............ *A61K 38/191* (2013.01); *A61K 47/10* (2013.01); *A61P 25/00* (2018.01); *C12N 5/0668* (2013.01)

(58) Field of Classification Search
CPC .... C12N 5/0668; A61K 47/10; A61K 38/191; A61P 25/00
See application file for complete search history.

(56) References Cited

U.S. PATENT DOCUMENTS

| | | | |
|---|---|---|---|
| 7,056,695 | B2 | 6/2006 | Dahiyat et al. |
| 7,101,974 | B2 | 9/2006 | Dahiyat et al. |
| 7,144,987 | B1 | 12/2006 | Chirino et al. |
| 7,244,823 | B2 | 7/2007 | Dahiyat et al. |
| 7,446,174 | B2 | 11/2008 | Desjarlais et al. |
| 7,662,367 | B2 | 2/2010 | Desjarlais et al. |
| 7,687,461 | B2 | 3/2010 | Desjarlais et al. |
| 11,365,299 | B2 | 6/2022 | Yagi |

OTHER PUBLICATIONS

Zhang et al., Site-directed mutational analysis of human tumor necrosis factor-alpha receptor binding site and structure-functional relationship, J Biol Chem 267(33) : 24069-24075(Nov. 1992) (Year: 1992).*
Burgess et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue J Cell Biol. 111:2129-2138 (Year: 1990).*
Lazar et al., Transforming Growth Factor : Mutation of Aspartic Acid 47 and Leucine 48 Results in Different Biological Activities Mol Cell Biol., 8:1247-1252, 1988 (Year: 1988).*
Bowie et al., Deciphering the message in Protein Sequences: Tolerance to Amino Acid Substitutions, Science, 247: 1306-1310 (Year: 1990).*
Whisstock et al., Prediction of protein function from protein sequence and structure, Quarterly Reviews Biophysics. 36(3):307-340, 2007 (Year: 2007).*
O'Callaghan et al. (2015), J. Neurochem 133(5):708-721 (Year: 2015).*
Nkiliza et al. (2021), Neuroscience Insights 16:1-11 (Year: 2021).*
The Commonwealth Nuerotrauma Initiative (CNI) Trust Fund Triennial Report, from Oct. 1, 2020 (Year: 2020).*
Steed et al. (2003). Inactivation of TNF signaling by rationally designed dominant-negative TNF variants. Science, 301 (5641), 1895-1898. DOI: 10.1126/science.1081297.
Zalevsky et al. (2007). Dominant-negative inhibitors of soluble TNF attenuate experimental arthritis without suppressing innate immunity to infection. The Journal of Immunology, 179(3), 1872-1883. DOI: 10.4049/jimmunol.179.3.1872.

* cited by examiner

*Primary Examiner* — Daniel E Kolker

(57) ABSTRACT

A method for treating Gulf War Illness (GWI) involves administering a therapeutically effective amount of a dominant negative tumor necrosis factor (DN-TNF) protein variant to a subject in need thereof. The DN-TNF variant is one that is modified with one to seven specific amino acid substitutions relative to the amino acid sequence of wtTNF and demonstrates a mechanism of selectively inhibiting soluble TNF (solTNF) without affecting transmembrane TNF (tmTNF) signaling. The method, exemplified by XPro1595 (pegipanermin), alleviates GWI symptoms, including depression, neuropathic pain, anxiety, and cognitive deficits, as shown in preclinical models. By targeting solTNF-driven neuroinflammation, this approach offers a novel therapeutic strategy for GWI.

8 Claims, 13 Drawing Sheets

Specification includes a Sequence Listing.

```
1        atgcaccacc  accaccacca  cgtacgctcc  tcctcccgca  ctccgtccga  caaaccggta
61       gctcacgtag  tagctaaccc  gcaggctgaa  ggtcagctgc  agtggctgaa  ccgccgcgct
121      aacgctctgc  tggctaacgg  tgtagaactg  cgcgacaacc  agctggtagt  accgtccgaa
181      ggtctgtacc  tgatctactc  ccaggtactg  ttcaaaggtc  agggttgtcc  gtccactcac
241      gtactgctga  ctcacactat  ctcccgcatc  gctgtatcct  accagactaa  agtaaacctg
301      ctgtccgcta  tcaaatcccc  gtgtcagcgc  gaaactccgg  aaggtgctga  agctaaaccg
361      tggtacgaac  cgatctacct  gggtggtgta  ttccagctgg  aaaaaggtga  ccgcctgtcc
421      gctgaaatca  accgcccgga  ctacctggac  ttcgctgaat  ccggtcaggt  atacttcggt
481      atcatcgctc  tgtga
```

(SEQ ID NO:1)

FIG.1A

```
1        MHHHHHHVRS  SSRTPSDKPV  AHVVANPQAE  GQLQWLNRRA  NALLANGVEL  RDNQLVVPSE
61       GLYLIYSQVL  FKGQGCPSTH  VLLTHTISRI  AVSYQTKVNL  LSAIKSPCQR  ETPEGAEAKP
121      WYEPIYLGGV  FQLEKGDRLS  AEINRPDYLD  FAESGQVYFG  IIAL
```

(SEQ ID NO:2)

FIG.1B

Val Arg Ser Ser Ser Arg Thr Pro Ser Asp Lys Pro Val Ala His Val Val Ala Asn Pro Gln Ala Glu
Gly Gln Leu Gln Trp Leu Asn Arg Arg Ala Asn Ala Leu Leu Ala Asn Gly Val Glu Leu Arg Asp
Asn Gln Leu Val Val Pro Ser Glu Gly Leu Tyr Leu Ile Tyr Ser Gln Val Leu Phe Lys Gly Gln
Gly Cys Pro Ser Thr His Val Leu Leu Thr His Thr Ile Ser Arg Ile Ala Val Ser Tyr Gln Thr Lys
Val Asn Leu Leu Ser Ala Ile Lys Ser Pro Cys Gln Arg Glu Thr Pro Glu Gly Ala Glu Ala Lys Pro
Trp Tyr Glu Pro Ile Thr Leu Gly Gly Val Phe Gln Leu Glu Lys Gly Asp Arg Leu Ser Ala Glu Ile
Asn Arg Pro Asp Tyr Leu Asp Phe Ala Glu Ser Gly Gln Val Tyr Phe Gly Ile Ile Ala Leu (SEQ ID NO:3)

FIG.1C

| Wild-type TNF amino acid | Wild-type TNF amino acid number | Mutants Created |
|---|---|---|
| Q | 21 | R |
| N | 30 | D |
| R | 31 | I, D, E |
| R | 32 | D, E, S |
| A | 33 | E |
| A | 35 | S |
| K | 65 | D, T, M, W, I, Q, S, N, V, E |
| G | 66 | Q, K |
| Q | 67 | D, W, Y, R, K, S |
| A | 111 | R, E |
| K | 112 | D, E |
| Y | 115 | Q, K, E, N, R, F, H, M, L, I, W, D, T, S |
| D | 140 | R, K |
| D | 143 | E, N, Q, S, R, K |
| F | 144 | N |
| A | 145 | R, D, K, N, H, T, Q, E, Y, M, S, F |
| E | 146 | N, K, R, S |
| S | 147 | R |

FIG.2

SPT

Hind paw
Mechanical hypersensitivity

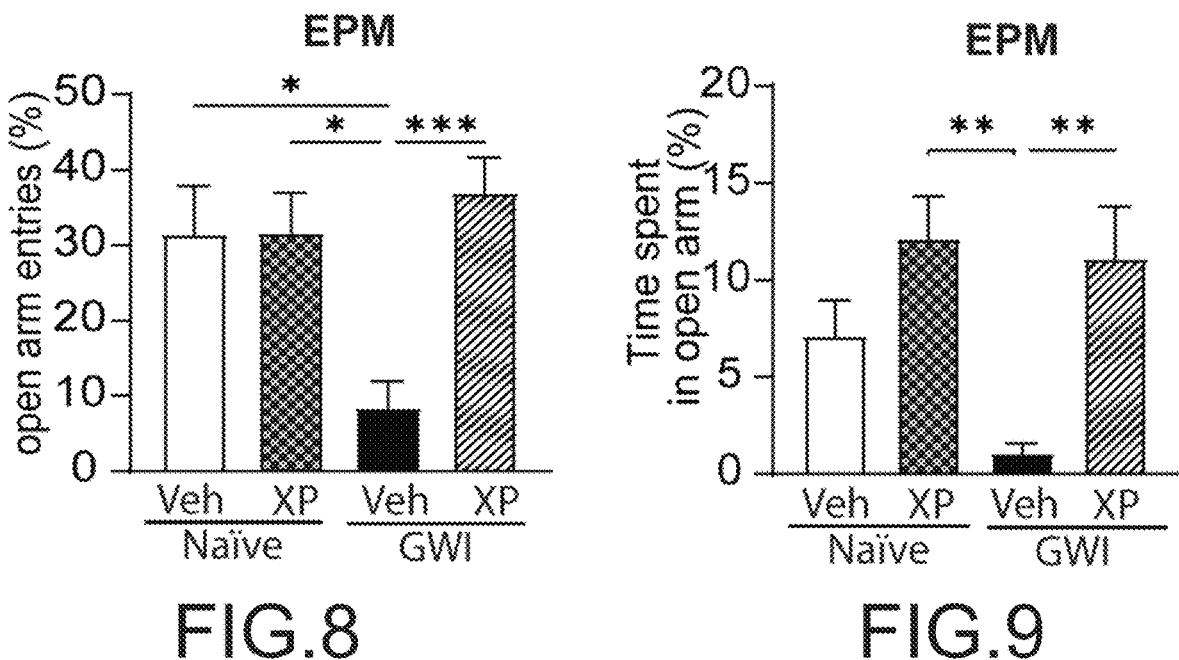
FIG.8
FIG.9
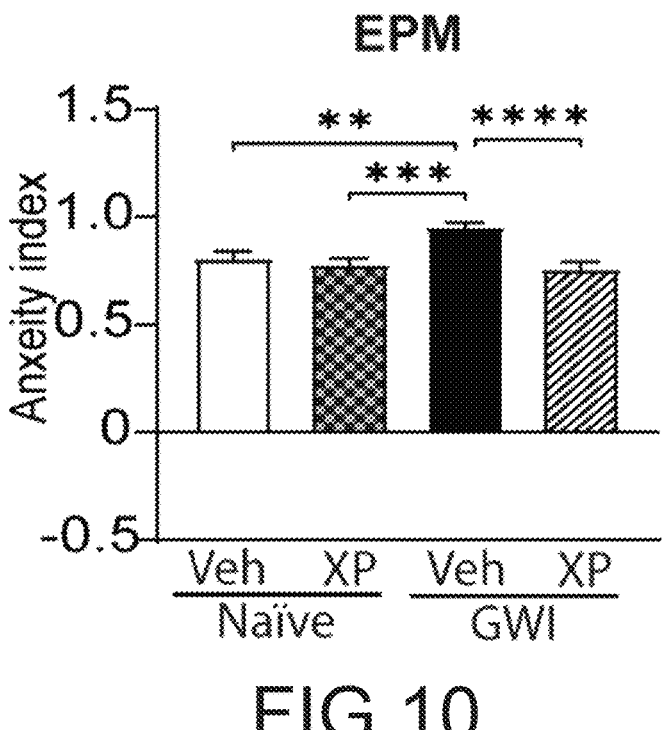
FIG.10

BM Probe test

BM Probe test

TREATMENT OF GULF WAR ILLNESS

CROSS-REFERENCE TO RELATED APPLICATIONS

This application claims benefit of priority with U.S. Provisional Application Ser. No. 63/244,469, filed Sep. 15, 2021; the entire contents of which are hereby incorporated by reference for all purposes.

GOVERNMENT LICENSE RIGHTS

This invention was made with government support under grant number W81XWH-20-1-0420 awarded by the Defense Health Agency (DHA/MRDB). The government has certain rights in the invention.

SEQUENCE LISTING

The contents of the electronic sequence listing (sequence-listing.xml; Size: 4,469 bytes; and Date of Creation: Mar. 9, 2023) is herein incorporated by reference in its entirety.

TECHNICAL FIELD

The invention is directed to a second medical use of a dominant negative tumor necrosis factor (DN-TNF) protein variant, or a method of medical treatment, applied to a subject suffering from Chronic Multisystem Illness (CMI), and more particularly, Gulf War Illness (GWI).

In one aspect, the invention is directed to a method of treating CMI, and more particularly GWI, in a subject in need thereof by administering a selective inhibitor of soluble tumor necrosis factor (solTNF), and more particularly, wherein the selective inhibitor of solTNF includes a dominant negative tumor necrosis alpha (DN-TNF) protein variant or a nucleic acid encoding the DN-TNF protein variant.

In another aspect, the invention is directed to a composition comprising a DN-TNF protein variant or a nucleic acid encoding the DN-TNF protein variant for use in treating a subject suffering from CMI, and more particularly, GWI.

BACKGROUND ART

Gulf War Illness (GWI) is a term that refers to a group of unexplained or ill-defined chronic symptoms found in Veterans deployed to the Persian Gulf during Operation Desert Storm/Operation Desert Shield (1990-1991). GWI falls under the umbrella of chronic multisystem illness (CMI).

Despite much research, the causes of GWI remain unclear. A number of possible causes of GWI include immune dysfunction, nerve dysfunction, mitochondrial dysfunction, and/or a genetic and environmental exposure interaction. During deployment, many service members encountered a variety of different exposures that may place them at risk for adverse health effects. Exposures specific for gulf war veterans include pyridostigmine bromide tablets (taken as a preventative measure), burning oil well fires, and the Anthrax Vaccination. There have been no clear or consistent links found between specific exposures and GWI. While several mental health conditions are often comorbid with GWI, GWI is not considered a mental health condition nor is GWI considered to be a result of malingering.

Symptoms of GWI vary; there is not a single consistent pattern of symptoms. This may make it challenging for healthcare providers to recognize and treat it. The most common symptoms of GWI include fatigue, muscle and joint pain, cognitive trouble, skin rashes, abdominal discomfort/bowel changes, headaches, shortness of breath, and sleep disturbances. It has been shown that about one-third of Gulf War Veterans (GWV) have GWI.

GWI falls under a broader umbrella term for a constellation of chronic, unexplained symptoms referred to as CMI and therefore treatment is similar.

Patients with CMI or GWI may be treated with pharmacologic agents that are also used to treat for other conditions. Often, the mechanisms of action of the pharmacologic agents are unknown. For example, patients who have fibromyalgia may benefit from duloxetine, which works independently of depression (which duloxetine is often prescribed for). Such agents include selective serotonin reuptake inhibitors, serotonin—norepinephrine reuptake inhibitors (for example, duloxetine), tricyclic medications (for example, amitriptyline), monoamine oxidase inhibitors (for example, phenelzine), dopaminergic blockers (for example, haloperidol), anxiolytics (for example, benzodiazepines), and medications that potentiate gaba-ergic transmission (for example, gabapentin), potentiate binding of voltage-gated calcium channels (for example, pregabalin), and potentiate voltage-dependent sodium channels (for example, topiramate). Analgesic medications include nonsteroidal anti-inflammatory analgesics, acetaminophen, opioid analgesics, and tramadol, which is serotonergic and partially binds to the mu-opiate receptor.

SUMMARY OF INVENTION

Technical Problem

There is no available cure for GWI. Pharmacologic agents that are available are generally have off target effects or are immunosuppressive. There is a need for a pharmacologic agent that is not immunosuppressive, preferably that crosses the blood brain barrier for treating the central nervous system and is efficacious for reducing signs and symptoms of GWI in the treated subject.

Solution to Problem

A solution to the aforementioned problem, and other problems that would be appreciated by one having skill in the art, may include, inter alia, use of a composition or implementation of a method including selective inhibition of soluble TNF (solTNF), including for example and not limitation, administration of a dominant negative TNF variant protein that: (i) crosses the blood brain barrier (BBB) in therapeutic amount, (ii) does not inhibit transmembrane TNF (tmTNF) and TNFR signaling, and (iii) is not immunosuppressive. Use of any selective inhibitor of the solubilized form of TNF is within the scope of the claimed invention; however, the biologic known as XPro1595 (a.k.a. "XPro"), also known as pegipanermin, a pegylated DN-TNF variant protein, or other DN-TNF variant protein may be preferred.

XPro is a variant protein of native TNF with six amino acid substitutions consisting of V1M, R31C, C69V, Y87H, C101A, and A145R, Another DN-TNF protein variant that can be similarly implemented is XENP346, which is a variant protein of native TNF comprising the amino acid substitutions I97T and A145R, As is described herein, any DN-TNF protein variant that arrests solTNF in a heterotrimer, blocking solTNF signaling without blocking transmembrane TNF (tmTNF) signaling, thereby having the same or similar mechanism of action, can be similarly implemented. Such DN-TNF variant protein is preferably modified with a pharmacokinetic enhancing moiety, such as polyethylene-glycol (PEG) or similar PK-enhancing compound.

Other features and aspects concerning the invention and/ or solutions to the problems will be recognized by one having skill in the art upon a thorough review of the appended details and descriptions, in particular when reviewed in conjunction with the enclosed drawings.

Advantageous Effects of Invention

DN-TNF variant proteins are created from a native TNF protein backbone, with select amino acid substitutions, rendering a DN-TNF variant protein that is substantially similar to native TNF. However, the DN-TNF protein variant is one that has dominant affinity for TNF trimerization, and is therefore able to dissociate a native TNF homotrimer and insert itself as a molecular component forming a TNF heterotrimer with solTNF monomer. The resulting heterotrimer is further characterized as lacking affinity for the TNF receptors, particularly TNFR1. By this mechanism, DN-TNF is capable of arresting solTNF in the patient, preventing solTNF-TNFR signaling, and freeing the TNFRs for promoting and polarizing transmembrane tmTNF-TNFR signaling, which is necessary to restore a homeostatic immune state in an inflamed patient. Attenuating inflammation allows the immune system to restore itself, and recover from a dysfunctional state.

BRIEF DESCRIPTION OF DRAWINGS

FIG. 1A shows the nucleic acid sequence of human TNF (SEQ ID NO:1). An additional six histidine codons, located between the start codon and the first amino acid, are underlined.

FIG. 1B shows the amino acid sequence of human TNF (SEQ ID NO:2) with an additional 6 histidines (underlined) between the start codon and the first amino acid. Amino acids changed in exemplary TNF-α variants are shown in bold.

FIG. 1C shows the amino acid sequence of human TNF-α (SEQ ID NO:3).

FIG. 2 shows the positions and amino acid changes in certain DN-TNF variants.

FIGS. 8-10 show results of an elevated plus maze test for the various experimental groups.

DESCRIPTION OF EMBODIMENTS

Figure 3:
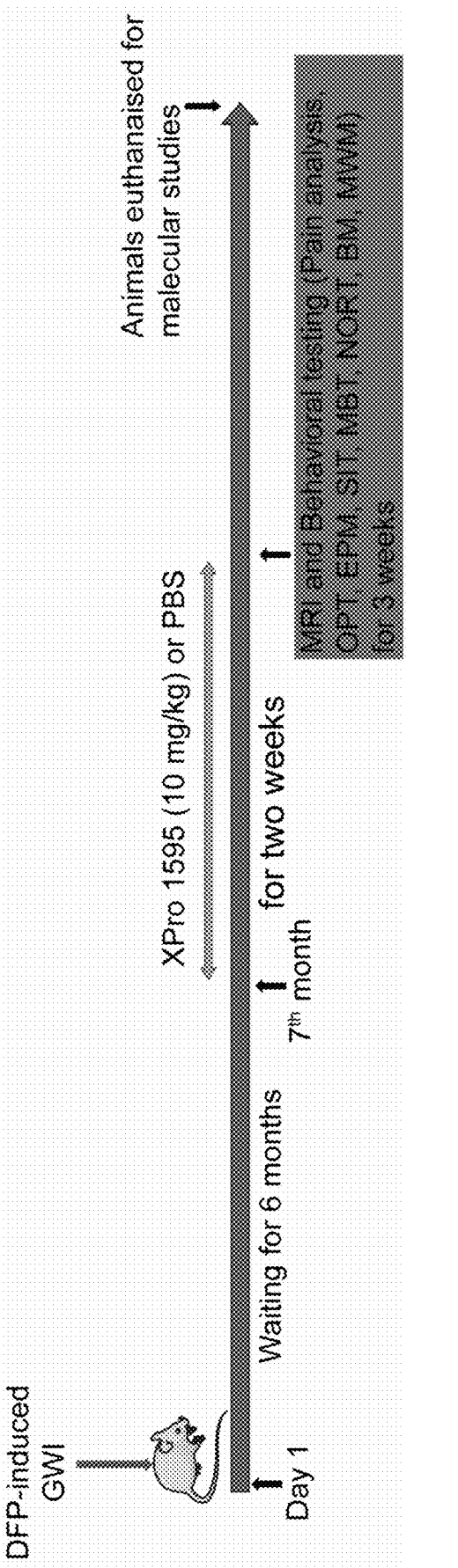
FIG. 3 shows a schematic of experiments investigating the effects of the DN-TNF protein variant XPro1595 on GWI-induced mice.

Disclosed herein is the novel and unexpected finding that selective neutralization of soluble tumor necrosis factor (solTNF), by systemic administration of a DN-TNF protein variant following GWI induced in mice, achieved: (i) improved depression compared to untreated subjects; (ii) improved neuropathic pain compared to untreated subjects; (iii) improved anxiety compared to untreated subjects; (iv) improved cognition compared to untreated subjects; (v) improved memory compared to untreated subjects; and (vi) improved biology compared to untreated subjects. A method that applies this unexpected finding is disclosed, and comprises the step of: administering, to a subject suffering from chronic multisystem illness, particularly gulf war illness, a therapeutically effective amount of a selective inhibitor of solTNF, such as a DN-TNF-α protein variant or a nucleic acid encoding the DN-TNF-α protein variant, for example, the DN-TNF-α protein known as XPro1595.

Selective Inhibitors of Soluble Tumor Necrosis Factor

Proteins with TNF-α antagonist activity, and nucleic acids encoding these proteins, were previously discovered which function to inhibit or otherwise neutralize the soluble form of TNF (solTNF) without inhibiting transmembrane TNF (tmTNF); collectively these proteins and nucleic acids encoding these proteins are herein collectively referred to as "selective inhibitors of solTNF".

Examples of selective inhibitors of solTNF are disclosed in U.S. Pat. Nos. 7,056,695; 7,101,974; 7,144,987; 7,244, 823; 7,446,174; 7,662,367; 7,687,461; and 11,365,229; the entire contents of each of which is hereby incorporated by reference.

Preferred selective inhibitors of solTNF may be dominant negative TNF proteins, referred to herein as "DNTNF," "DN-TNF protein variants," "TNF variants," "TNF variant proteins," "variant TNF," "variant TNF," and the like. By "variant TNF" or "TNF proteins" is meant TNFα or TNF proteins that differ from the corresponding wild type protein by at least 1 amino acid. Thus, a variant of human TNF is compared to SEQ ID NO:1 (nucleic acid including codons for 6 histidines), SEQ ID NO:2 (amino acid including 6 N-terminal histidines) or SEQ ID NO:3 (amino acid without 6 N-terminal histidines). DN-TNF protein variants are disclosed in detail in U.S. Pat. No. 7,446,174, which is incorporated herein in its entirety by reference. As used herein, variant TNF or TNF proteins include TNF monomers, dimers or trimers. Included within the definition of "variant TNF" are competitive inhibitor TNF variants. While certain variants as described herein, one having skill in the art will understand that other variants may be made while retaining the function of inhibiting soluble but not transmembrane TNF.

Thus, the proteins useful in various aspects of the invention are antagonists of wild type TNF. By "antagonists of wild type TNF" is meant that the variant TNF protein inhibits or significantly decreases at least one biological activity of wild-type TNF.

In a preferred embodiment the variant is antagonist of soluble TNF, but does not significantly antagonize transmembrane TNF, e.g., DN-TNF protein as disclosed herein inhibits signaling by soluble TNF, but not transmembrane TNF. By "inhibits the activity of TNF" and grammatical equivalents is meant at least a 10% reduction in wild-type, soluble TNF, more preferably at least a 50% reduction in wild-type, soluble TNF activity, and even more preferably, at least 90% reduction in wild-type, soluble TNF activity. Preferably there is an inhibition in wild-type soluble TNF activity in the absence of reduced signaling by transmembrane TNF. In a preferred embodiment, the activity of soluble TNF is inhibited while the activity of transmembrane TNF is substantially and preferably completely maintained.

The TNF proteins useful in various embodiments of the invention have modulated activity as compared to wild type proteins. In a preferred embodiment, variant TNF proteins exhibit decreased biological activity (e.g. antagonism) as compared to wild type TNF, including but not limited to, decreased binding to a receptor (p55, p75 or both), decreased activation and/or ultimately a loss of cytotoxic activity. By "cytotoxic activity" herein refers to the ability of a TNF variant to selectively kill or inhibit cells. Variant TNF proteins that exhibit less than 50% biological activity as compared to wild type are preferred. More preferred are variant TNF proteins that exhibit less than 25%, even more preferred are variant proteins that exhibit less than 15%, and most preferred are variant TNF proteins that exhibit less than 10% of a biological activity of wild-type TNF. Suitable assays include, but are not limited to, caspase assays, TNF cytotoxicity assays, DNA binding assays, transcription assays (using reporter constructs), size exclusion chromatography assays and radiolabeling/immuno-precipitation), and stability assays (including the use of circular dichroism (CD) assays and equilibrium studies), according to methods know in the art.

In one embodiment, at least one property critical for binding affinity of the variant TNF proteins is altered when compared to the same property of wild type TNF and in particular, variant TNF proteins with altered receptor affinity are preferred. Particularly preferred are variant TNF with altered affinity toward oligomerization to wild type TNF. Thus, the invention makes use of variant TNF proteins with altered binding affinities such that the variant TNF proteins will preferentially oligomerize with wild type TNF, but do not substantially interact with wild type TNF receptors, i.e., p55, p75. "Preferentially" in this case means that given equal amounts of variant TNF monomers and wild type TNF monomers, at least 25% of the resulting trimers are mixed trimers of variant and wild type TNF, with at least about 50% being preferred, and at least about 80-90% being particularly preferred. In other words, it is preferable that the variant TNF proteins implemented in embodiments of the invention have greater affinity for wild type TNF protein as compared to wild type TNF proteins. By "do not substantially interact with TNF receptors" is meant that the variant TNF proteins will not be able to associate with either the p55 or p75 receptors to significantly activate the receptor and initiate the TNF signaling pathway(s). In a preferred embodiment, at least a 50% decrease in receptor activation is seen, with greater than 50%, 75%, 80-90% being preferred.

In some embodiments, the variants of the invention are antagonists of both soluble and transmembrane TNF. However, as described herein, preferred variant TNF proteins are antagonists of the activity of soluble TNF but do not substantially affect the activity of transmembrane TNF. Thus, a reduction of activity of the heterotrimers for soluble TNF is as outlined above, with reductions in biological activity of at least 10%, 25, 50, 75, 80, 90, 95, 99 or 100% all being preferred. However, some of the variants outlined herein comprise selective inhibition; that is, they inhibit soluble TNF activity but do not substantially inhibit transmembrane TNF. In these embodiments, it is preferred that at least 80%, 85, 90, 95, 98, 99 or 100% of the transmembrane TNF activity is maintained. This may also be expressed as a ratio; that is, selective inhibition can include a ratio of inhibition of soluble to transmembrane TNF. For example, variants that result in at least a 10:1 selective inhibition of soluble to transmembrane TNF activity are preferred, with 50:1, 100:1, 200:1, 500:1, 1000:1 or higher find particular use in the invention. Thus, one embodiment utilizes variants, such as double mutants at positions 87/145 as outlined herein, that substantially inhibit or eliminate soluble TNF activity (for example by exchanging with homotrimeric wild-type to form heterotrimers that do not bind to TNF receptors or that bind but do not activate receptor signaling) but do not significantly affect (and preferably do not alter at all) transmembrane TNF activity. Without being bound by theory, the variants exhibiting such differential inhibition allow the decrease of inflammation without a corresponding loss in immune response.

In one embodiment, the affected biological activity of the variants is the activation of receptor signaling by wild type TNF proteins. In a preferred embodiment, the variant TNF protein interacts with the wild type TNF protein such that the complex comprising the variant TNF and wild type TNF has reduced capacity to activate (as outlined above for "substantial inhibition"), and in preferred embodiments is incapable of activating, one or both of the TNF receptors, i.e. p55 TNF-R (TNFR1) or p75 TNF-R (TNFR2). In a preferred embodiment, the variant TNF protein is a variant TNF protein that functions as an antagonist of wild type TNF. Preferably, the variant TNF protein preferentially interacts with wild type TNF to form mixed trimers with the wild type protein such that receptor binding does not significantly occur and/or TNF signaling is not initiated. By mixed trimers is meant that monomers of wild type and variant TNF proteins interact to form heterotrimeric TNF. Mixed trimers may comprise 1 variant TNF protein:2 wild type TNF proteins, 2 variant TNF proteins:1 wild type TNF protein. In some embodiments, trimers may be formed comprising only variant TNF proteins.

The variant TNF antagonist proteins implemented in embodiments of the invention are highly specific for TNF antagonism relative to TNF-beta antagonism. Additional characteristics include improved stability, pharmacokinetics, and high affinity for wild type TNF. Variants with higher affinity toward wild type TNF may be generated from variants exhibiting TNF antagonism as outlined above.

Similarly, variant TNF proteins, for example are experimentally tested and validated in in vivo and in in vitro assays. Suitable assays include, but are not limited to, activity assays and binding assays. For example, TNF activity assays, such as detecting apoptosis via caspase activity can be used to screen for TNF variants that are antagonists of wild type TNF. Other assays include using the Sytox green nucleic acid stain to detect TNF-induced cell permeability in an Actinomycin-D sensitized cell line. As this stain is excluded from live cells, but penetrates dying cells, this assay also can be used to detect TNF variants that are agonists of wild-type TNF. By "agonists of wild type TNF" is meant that the variant TNF protein enhances the activation of receptor signaling by wild type TNF proteins. Generally, variant TNF proteins that function as agonists of wild type TNF are not preferred. However, in some embodiments, variant TNF proteins that function as agonists of wild type TNF protein are preferred. An example of an NF kappaB assay is presented in Example 7 of U.S. Pat. No. 7,446,174, which is expressly incorporated herein by reference.

In a preferred embodiment, binding affinities of variant TNF proteins as compared to wild type TNF proteins for naturally occurring TNF and TNF receptor proteins such as p55 and p75 are determined. Suitable assays include, but are not limited to, e.g., quantitative comparisons comparing kinetic and equilibrium binding constants, as are known in the art. Examples of binding assays are described in Example 6 of U.S. Pat. No. 7,446,174, which is expressly incorporated herein by reference.

In a preferred embodiment, the variant TNF protein has an amino acid sequence that differs from a wild type TNF sequence by at least 1 amino acid, with from 1, 2, 3, 4, 5, 6, 7, 8, 9 and 10 amino acids all contemplated, or higher. Expressed as a percentage, the variant TNF proteins of the invention preferably are greater than 90% identical to wild-type, with greater than 95, 97, 98 and 99% all being contemplated. Stated differently, based on the human TNF sequence of FIG. 1B (SEQ ID NO:2) excluding the N-terminal 6 histidines, as shown in FIG. 1C (SEQ ID NO:3), variant TNF proteins have at least about 1 residue that differs from the human TNF sequence, with at least about 2, 3, 4, 5, 6, 7 or 8 different residues. Preferred variant TNF proteins have 3 to 8 different residues.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). In a similar manner, "percent (%) nucleic acid sequence identity" with respect to the coding sequence of the polypeptides identified is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

TNF proteins may be fused to, for example, other therapeutic proteins or to other proteins such as Fc or serum albumin for therapeutic or pharmacokinetic purposes. In this embodiment, a TNF protein implemented in embodiments of the invention is operably linked to a fusion partner. The fusion partner may be any moiety that provides an intended therapeutic or pharmacokinetic effect. Examples of fusion partners include but are not limited to Human Serum Albumin, a therapeutic agent, a cytotoxic or cytotoxic molecule, radionucleotide, and an Fc, etc. As used herein, an Fc fusion is synonymous with the terms "immunoadhesin", "Ig fusion", "Ig chimera", and "receptor globulin" as used in the prior art (Chamow et al., 1996, Trends Biotechnol 14:52-60; Ashkenazi et al., 1997, Curr Opin Immunol 9:195-200, both incorporated by reference). An Fc fusion combines the Fc region of an immunoglobulin with the target-binding region of a TNF protein, for example. See for example U.S. Pat. Nos. 5,766,883 and 5,876,969, both of which are hereby incorporated by reference.

In a preferred embodiment, the variant TNF proteins comprise variant residues selected from the following positions 21, 23, 30, 31, 32, 33, 34, 35, 57, 65, 66, 67, 69, 75, 84, 86, 87, 91, 97, 101, 111, 112, 115, 140, 143, 144, 145, 146, and 147. Preferred amino acids for each position, including the human TNF residues, are shown in FIG. 2. Thus, for example, at position 143, preferred amino acids are Glu, Asn, Gln, Ser, Arg, and Lys; etc. Preferred changes include: V1M, Q21C, Q21R, E23C, R31C, N34E, V91E, Q21R, N30D, R31C, R31I, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, C101A, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R. These may be done either individually or in combination, with any combination being possible. However, as outlined herein, preferred embodiments utilize at least 1 to 8, and preferably more, positions in each variant TNF protein.

In an additional aspect, the invention provides TNF variants selected from the group consisting of XENP268 XENP344, XENP345, XENP346, XENP550, XENP551, XENP557, XENP1593, XENP1594, and XENP1595 as outlined in Example 3 OF U.S. Pat. No. 7,662,367, which is incorporated herein by reference.

In an additional aspect, the invention makes use of methods of forming a TNF heterotrimer in vivo in a mammal comprising administering to the mammal a variant TNF molecule as compared to the corresponding wild-type mammalian TNF, wherein said TNF variant is substantially free of agonistic activity.

In an additional aspect, the invention makes use of methods of screening for selective inhibitors comprising contacting a candidate agent with a soluble TNF protein and assaying for TNF biological activity; contacting a candidate agent with a transmembrane TNF protein and assaying for TNF biological activity, and determining whether the agent is a selective inhibitor. The agent may be a protein (including peptides and antibodies, as described herein) or small molecules.

In a further aspect, the invention makes use of variant TNF proteins that interact with the wild type TNF to form mixed trimers incapable of activating receptor signaling. Preferably, variant TNF proteins with 1, 2, 3, 4, 5, 6 and 7 amino acid changes are used as compared to wild type TNF protein. In a preferred embodiment, these changes are selected from positions 1, 21, 23, 30, 31, 32, 33, 34, 35, 57, 65, 66, 67, 69, 75, 84, 86, 87, 91, 97, 101, 111, 112, 115, 140, 143, 144, 145, 146 and 147. In an additional aspect, the non-naturally occurring variant TNF proteins have substitutions selected from the group of substitutions consisting of: V1M, Q21C, Q21R, E23C, N30D, R31C, R31I, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, C101A, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R.

In another preferred embodiment, substitutions may be made either individually or in combination, with any combination being possible. Preferred embodiments utilize at least one, and preferably more, positions in each variant TNF protein. For example, substitutions at positions 31, 57, 69, 75, 86, 87, 97, 101, 115, 143, 145, and 146 may be combined to form double variants. In addition, triple, quadruple, quintuple and the like, point variants may be generated.

In one aspect the invention makes use of TNF variants comprising the amino acid substitutions A145R/I97T. In one aspect, the invention provides TNF variants comprising the amino acid substitutions V1M, R31C, C69V, Y87H, C101A, and A145R. In a preferred embodiment, this variant is PEGylated.

In a preferred embodiment the variant is XPRO1595, a PEGylated protein comprising V1M, R31C, C69V, Y87H, C101A, and A145R mutations relative to the wild type human sequence, also referred to as "XPro".

For purposes of the present invention, the areas of the wild type or naturally occurring TNF molecule to be modified are selected from the group consisting of the Large Domain (also known as II), Small Domain (also known as I), the DE loop, and the trimer interface. The Large Domain, the Small Domain and the DE loop are the receptor interaction domains. The modifications may be made solely in one of these areas or in any combination of these areas. The Large Domain preferred positions to be varied include: 21, 30, 31, 32, 33, 35, 65, 66, 67, 111, 112, 115, 140, 143, 144, 145, 146 and/or 147. For the Small Domain, the preferred positions to be modified are 75 and/or 97. For the DE Loop, the preferred position modifications are 84, 86, 87 and/or 91. The Trimer Interface has preferred double variants including positions 34 and 91 as well as at position 57. In a preferred embodiment, substitutions at multiple receptor interaction and/or trimerization domains may be combined. Examples include, but are not limited to, simultaneous substitution of amino acids at the large and small domains (e.g. A145R and I97T), large domain and DE loop (A145R and Y87H), and large domain and trimerization domain (A145R and L57F). Additional examples include any and all combinations, e.g., I97T and Y87H (small domain and DE loop). More specifically, theses variants may be in the form of single point variants, for example K112D, Y115K, Y115I, Y115T, A145E or A145R. These single point variants may be combined, for example, Y115I and A145E, or Y115I and A145R, or Y115T and A145R or Y115I and A145E; or any other combination.

Preferred double point variant positions include 57, 75, 86, 87, 97, 115, 143, 145, and 146; in any combination. In addition, double point variants may be generated including L57F and one of Y115I, Y115Q, Y115T, D143K, D143R, D143E, A145E, A145R, E146K or E146R. Other preferred double variants are Y115Q and at least one of D143N, D143Q, A145K, A145R, or E146K; Y115M and at least one of D143N, D143Q, A145K, A145R or E146K; and L57F and at least one of A145E or 146R; K65D and either D143K or D143R, K65E and either D143K or D143R, Y115Q and any of L75Q, L57W, L57Y, L57F, I97R, I97T, S86Q, D143N, E146K, A145R and I97T, A145R and either Y87R or Y87H; N34E and V91E; L75E and Y115Q; L75Q and Y115Q; L75E and A145R; and L75Q and A145R.

Further, triple point variants may be generated. Preferred positions include 34, 75, 87, 91, 115, 143, 145 and 146. Examples of triple point variants include V91E, N34E and one of Y115I, Y115T, D143K, D143R, A145R, A145E E146K, and E146R. Other triple point variants include L75E and Y87H and at least one of Y115Q, A145R, Also, L75K, Y87H and Y115Q. More preferred are the triple point variants V91E, N34E and either A145R or A145E.

Variant TNF proteins may also be identified as being encoded by variant TNF nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred. In a preferred embodiment, a variant TNF nucleic acid encodes a variant TNF protein. As will be appreciated by those in the art, due to the degeneracy of the genetic code, an extremely large number of nucleic acids may be made, all of which encode the variant TNF proteins of the present invention. Thus, having identified a particular amino acid sequence, those skilled in the art could make any number of different nucleic acids, by simply modifying the sequence of one or more codons in a way which does not change the amino acid sequence of the variant TNF.

In one embodiment, the nucleic acid homology is determined through hybridization studies. Thus, for example, nucleic acids which hybridize under high stringency to the nucleic acid sequence shown in FIG. 1A (SEQ ID NO:1) or its complement and encode a variant TNF protein is considered a variant TNF gene. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993), incorporated by reference. Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra. In addition, nucleic acid variants encode TNF protein variants comprising the amino acid substitutions described herein. In one embodiment, the TNF variant encodes a polypeptide variant comprising the amino acid substitutions A145R/197T. In one aspect, the nucleic acid variant encodes a polypeptide comprising the amino acid substitutions V1M, R31C, C69V, Y87H, C101A, and A145R, or any 1, 2, 3, 4 or 5 of these variant amino acids.

The variant TNF proteins and nucleic acids of the present invention are recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half-life of such molecules in physiological environments. The nucleic acid may be double stranded, single stranded, or contain portions of both double stranded or single stranded sequence. As will be appreciated by those in the art, the depiction of a single strand ("Watson") also defines the sequence of the other strand ("Crick"); thus, the sequence depicted in FIG. 1A (SEQ ID NO:1) also includes the complement of the sequence. By the term "recombinant nucleic acid" is meant nucleic acid, originally formed in vitro, in general, by the manipulation of nucleic acid by endonucleases, in a form not normally found in nature. Thus, an isolated variant TNF nucleic acid, in a linear form, or an expression vector formed in vitro by ligating DNA molecules that are not normally joined, are both considered recombinant for the purposes of this invention.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild-type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a variant TNF protein from one organism in a different organism or host cell. Alternatively, the protein may be made at a significantly higher concentration than is normally seen, through the use of an inducible promoter or high expression promoter, such that the protein is made at increased concentration levels. Furthermore, all of the variant TNF proteins outlined herein are in a form not normally found in nature, as they contain amino acid substitutions, insertions and deletions, with substitutions being preferred, as discussed below.

Also included within the definition of variant TNF proteins of the present invention are amino acid sequence variants of the variant TNF sequences outlined herein and shown in the Figures. That is, the variant TNF proteins may contain additional variable positions as compared to human TNF. These variants fall into one or more of three classes: substitutional, insertional or deletional variants.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Using the nucleic acids disclosed herein, which encode a variant TNF protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the variant TNF protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein or of the variant TNF protein, a replacement of the naturally occurring secretory leader sequence is desired. In this embodiment, an unrelated secretory leader sequence is operably linked to a variant TNF encoding nucleic acid leading to increased protein secretion. Thus, any secretory leader sequence resulting in enhanced secretion of the variant TNF protein, when compared to the secretion of TNF and its secretory sequence, is desired. Suitable secretory leader sequences that lead to the secretion of a protein are known in the art. In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from *Bacillus* are preferably used to express the fusion protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences. Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences that flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used. A preferred expression vector system is a retroviral vector system such as is generally described in PCT/US97/01019 and PCT/US97/01048, both of which are hereby incorporated by reference. In a preferred embodiment, the expression vector comprises the components described above and a gene encoding a variant TNF protein. As will be appreciated by those in the art, all combinations are possible and accordingly, as used herein, the combination of components, comprised by one or more vectors, which may be retroviral or not, is referred to herein as a "vector composition".

A number of viral based vectors have been used for gene delivery. See for example U.S. Pat. No. 5,576,201, which is expressly incorporated herein by reference. For example, retroviral systems are known and generally employ packaging lines which have an integrated defective provirus (the "helper") that expresses all of the genes of the virus but cannot package its own genome due to a deletion of the packaging signal, known as the psi sequence. Thus, the cell line produces empty viral shells. Producer lines can be derived from the packaging lines which, in addition to the helper, contain a viral vector, which includes sequences required in cis for replication and packaging of the virus, known as the long terminal repeats (LTRs). The gene of interest can be inserted in the vector and packaged in the viral shells synthesized by the retroviral helper. The recombinant virus can then be isolated and delivered to a subject. (See, e.g., U.S. Pat. No. 5,219,740.) Representative retroviral vectors include but are not limited to vectors such as the LHL, N2, LNSAL, LSHL and LHL2 vectors described in e.g., U.S. Pat. No. 5,219,740, incorporated herein by reference in its entirety, as well as derivatives of these vectors. Retroviral vectors can be constructed using techniques well known in the art. See, e.g., U.S. Pat. No. 5,219,740; Mann et al. (1983) Cell 33:153-159.

Adenovirus based systems have been developed for gene delivery and are suitable for delivery according to the methods described herein. Human adenoviruses are double-stranded DNA viruses that enter cells by receptor-mediated endocytosis. These viruses are particularly well suited for gene transfer because they are easy to grow and manipulate and they exhibit a broad host range in vivo and in vitro.

Adenoviruses infect quiescent as well as replicating target cells. Unlike retroviruses which integrate into the host genome, adenoviruses persist extrachromosomally thus minimizing the risks associated with insertional mutagenesis. The virus is easily produced at high titers and is stable so that it can be purified and stored. Even in the replication-competent form, adenoviruses cause only low-level morbidity and are not associated with human malignancies. Accordingly, adenovirus vectors have been developed which make use of these advantages. For a description of adenovirus vectors and their uses see, e.g., Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; Rich et al. (1993) Human Gene Therapy 4:461-476.

In a preferred embodiment, the viral vectors used in the subject methods are AAV vectors. By an "AAV vector" is meant a vector derived from an adeno-associated virus serotype, including without limitation, AAV-1, AAV-2, AAV-3, AAV-4, AAV-5, AAVX7, etc. Typical AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. An AAV vector includes at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. For more on various AAV serotypes, see for example Cearley et al., Molecular Therapy, 16:1710-1718, 2008, which is expressly incorporated herein in its entirety by reference.

AAV expression vectors may be constructed using known techniques to provide as operatively linked components in the direction of transcription, control elements including a transcriptional initiation region, the DNA of interest and a transcriptional termination region. The control elements are selected to be functional in a thalamic and/or cortical neuron. Additional control elements may be included. The resulting construct, which contains the operatively linked components is bounded (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, R. M. (1994) Human Gene Therapy 5:793-801; Berns, K. I. "Parvoviridae and their Replication" in Fundamental Virology, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV sero-types, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

Suitable DNA molecules for use in AAV vectors will include, for example, a gene that encodes a protein that is defective or missing from a recipient subject or a gene that encodes a protein having a desired biological or therapeutic effect (e.g., an enzyme, or a neurotrophic factor). The artisan of reasonable skill will be able to determine which factor is appropriate based on the neurological disorder being treated.

The selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomega-lovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially avail-able.

Once made, the TNF protein may be covalently modified. For instance, a preferred type of covalent modification of variant TNF comprises linking the variant TNF polypeptide to one of a variety of nonproteinaceous polymers, e.g., polyethylene glycol ("PEG"), polypropylene glycol, or polyoxyalkylenes, in the manner set forth in U.S. Pat. Nos. 4,640,835; 4,496,689; 4,301,144; 4,670,417; 4,791,192 or 4,179,337, incorporated by reference. These nonproteina-ceous polymers may also be used to enhance the variant TNF's ability to disrupt receptor binding, and/or in vivo stability. In another preferred embodiment, cysteines are designed into variant or wild type TNF in order to incorpo-rate (a) labeling sites for characterization and (b) incorporate PEGylation sites. For example, labels that may be used are well known in the art and include but are not limited to biotin, tag and fluorescent labels (e.g. fluorescein). These labels may be used in various assays as are also well known in the art to achieve characterization. A variety of coupling chemistries may be used to achieve PEGylation, as is well known in the art. Examples include but are not limited to, the technologies of Shearwater and Enzon, which allow modification at primary amines, including but not limited to, lysine groups and the N-terminus See, Kinstler et al, Advanced Drug Deliveries Reviews, 54, 477-485 (2002) and M J Roberts et al, Advanced Drug Delivery Reviews, 54, 459-476 (2002), both hereby incorporated by reference.

In one preferred embodiment, the optimal chemical modi-fication sites are 21, 23, 31 and 45, taken alone or in any combination. In an even more preferred embodiment, a TNF variant of the present invention includes the R31C mutation.

In a preferred embodiment, the variant TNF protein is purified or isolated after expression. Variant TNF proteins may be isolated or purified in a variety of ways known to those skilled in the art depending on what other components are present in the sample.

In another preferred embodiment, the TNF protein is administered via gene modified autologous or allogeneic cellular therapy, wherein the gene therapy comprises mes-enchymal stem cells expressing a construct of the TNF protein, preferably a DN-TNF protein, more preferably XPRO1595.

Treatment Methods

The terms "treatment", "treating", and the like, as used herein include amelioration or elimination of a disease or condition once it has been established or alleviation of the characteristic symptoms of such disease or condition. A method as disclosed herein may also be used to, depending on the condition of the patient, prevent the onset of a disease or condition or of symptoms associated with a disease or condition, including reducing the severity of a disease or condition or symptoms associated therewith prior to afflic-tion with said disease or condition. Such prevention or reduction prior to affliction refers to administration of the compound or composition as described herein to a patient that is not at the time of administration afflicted with the disease or condition. "Preventing" also encompasses pre-venting the recurrence or relapse-prevention of a disease or condition or of symptoms associated therewith, for instance after a period of improvement.

In one embodiment, a selective inhibitor of solTNF as described herein is administered peripherally to a patient in need thereof to reduce inflammation, improve cortical spar-ing and associated neurological outcome, mitigate injury induced by pathophysiological changes in the hippocampus, and/or attenuate cognitive impairment, pain- and depressive-like behaviors.

In one embodiment, the treatment method includes administering to the patient suffering from chronic multi-system illness, particularly gulf war illness, a therapeutically effective amount of a selective inhibitor of solTNF, such as a DN-TNF protein variant and/or a nucleic acid encoding the DN-TNF protein variant, for example and without limita-tion, the biologic known as XPro1595, whereby the patient is treated.

In some embodiments, the method may comprise subcu-taneous injection of the selective inhibitor of solTNF for treatment of gulf war illness.

In another embodiment, the method may comprise intra-venous administration of the selective inhibitor of solTNF for treatment of gulf war illness.

In an alternative embodiment the method may comprise topical administration of a selective inhibitor of solTNF as described herein. In this embodiment the DN-TNF may be formulated as a lotion or cream.

Other methods of administration are further described herein or may be appreciated by one having skill in the art.

Formulations

Depending upon the manner of introduction, the pharmaceutical composition may be formulated in a variety of ways. The concentration of the therapeutically active variant TNF protein in the formulation may vary from about 0.1 to 100 weight %. In another preferred embodiment, the concentration of the variant TNF protein is in the range of 0.003 to 1.0 molar, with dosages from 0.03, 0.05, 0.1, 0.2, and 0.3 millimoles per kilogram of body weight being preferred.

The pharmaceutical compositions for use in embodiments of the present invention comprise a variant TNF protein in a form suitable for administration to a patient. In the preferred embodiment, the pharmaceutical compositions are in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

Pharmaceutical compositions are contemplated wherein a TNF variant of the present invention and one or more therapeutically active agents are formulated. Formulations of the present invention are prepared for storage by mixing TNF variant having the desired degree of purity with optional pharmaceutically acceptable carriers, excipients or stabilizers (Remington's Pharmaceutical Sciences 16th edition, Osol, A. Ed., 1980, incorporated entirely by reference), in the form of lyophilized formulations or aqueous solutions. Lyophilization is well known in the art, see, e.g., U.S. Pat. No. 5,215,743, incorporated entirely by reference. Acceptable carriers, excipients, or stabilizers are nontoxic to recipients at the dosages and concentrations employed, and include buffers such as histidine, phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches;

binding agents; additives; coloring agents; salt-forming counter-ions such as sodium; metal complexes (e.g. Zn-protein complexes); and/or non-ionic surfactants such as TWEEN®, PLURONICS® or polyethylene glycol (PEG). In a preferred embodiment, the pharmaceutical composition that comprises the TNF variant of the present invention may be in a water-soluble form. The TNF variant may be present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

Controlled Release

In addition, any of a number of delivery systems are known in the art and may be used to administer TNF variants in accordance with embodiments of the present invention. Examples include, but are not limited to, encapsulation in liposomes, microparticles, microspheres (e.g. PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-gutamate, ethylene-vinyl acetate, lactic acid-glycolic acid copolymers such as the LUPRON DEPOT®, and poly-D-(–)-3-hydroxybutyric acid. It is also possible to administer a nucleic acid encoding the TNF of the current invention, for example by retroviral infection, direct injection, or coating with lipids, cell surface receptors, or other transfection agents. In all cases, controlled release systems may be used to release the TNF at or close to the desired location of action.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations. In a further embodiment, the variant TNF proteins are added in a micellular formulation; see U.S. Pat. No. 5,833,948, incorporated entirely by reference. Alternatively, liposomes may be employed with the TNF proteins to effectively deliver the protein. Combinations of pharmaceutical compositions may be administered. Moreover, the TNF compositions of the present invention may be administered in combination with other therapeutics, either substantially simultaneously or co-administered, or serially, as the need may be.

Dosage forms for the topical or transdermal administration of a DN-TNF protein disclosed herein include powders, sprays, ointments, pastes, creams, lotions, gels, solutions, patches and inhalants. The DN-TNF protein may be mixed under sterile conditions with a pharmaceutically-acceptable carrier, and with any preservatives, buffers, or propellants which may be required. Powders and sprays can contain, in addition to the DN-TNF protein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Methods of Administration

The administration of the selective inhibitor of solTNF in accordance with embodiments of the present invention, preferably in the form of a sterile aqueous solution, is done peripherally, in a variety of ways, including, but not limited to, orally, subcutaneously, intravenously, intranasally, transdermally, intraperitoneally, intramuscularly, intrapulmonary, vaginally, rectally, or intraocularly. In some instances, the selective inhibitor of solTNF may be directly applied as a solution, salve, cream or spray. The selective inhibitor of solTNF may also be delivered by bacterial or fungal expression into the human system (e.g., WO 04046346 A2, hereby incorporated by reference).

Subcutaneous

Subcutaneous administration may be preferable in some circumstances because the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate. A selective inhibitor of solTNF may be more amenable to subcutaneous administration due to, for example, increased potency, improved serum half-life, or enhanced solubility.

Intravenous

As is known in the art, protein therapeutics are often delivered by IV infusion or bolus. The selective inhibitor of solTNF may also be delivered using such methods. For example, administration may be by intravenous infusion with 0.9% sodium chloride as an infusion vehicle.

Inhaled

Pulmonary delivery may be accomplished using an inhaler or nebulizer and a formulation comprising an aerosolizing agent. For example, inhalable technology, or a pulmonary delivery system may be used. The selective inhibitor of solTNF may be more amenable to intrapulmonary delivery. The selective inhibitor of solTNF may also be more amenable to intrapulmonary administration due to, for example, improved solubility or altered isoelectric point.

Oral Delivery

Furthermore, the selective inhibitor of solTNF may be more amenable to oral delivery due to, for example, improved stability at gastric pH and increased resistance to proteolysis.

Transdermal

Transdermal patches may have the added advantage of providing controlled delivery of the selective inhibitor of solTNF to the body. Dissolving or dispersing DN-TNF protein in the proper medium can make such dosage forms. Absorption enhancers can also be used to increase the flux of DN-TNF protein across the skin. Either providing a rate controlling membrane or dispersing DN-TNF protein in a polymer matrix or gel can control the rate of such flux.

Intraocular

Ophthalmic formulations, eye ointments, powders, solutions and the like, are also contemplated as being suitable for use in embodiments of this invention.

In a preferred embodiment, the selective inhibitor of solTNF is administered as a therapeutic agent, and can be formulated as outlined above. Similarly, variant TNF genes (including both the full-length sequence, partial sequences, or regulatory sequences of the variant TNF coding regions) may be administered in gene therapy applications, as is known in the art. These variant TNF genes can include antisense applications, either as gene therapy (i.e. for incorporation into the genome) or as antisense compositions, as will be appreciated by those in the art.

Dosage

Dosage may be determined depending on the complication being treated and mechanism of delivery. Typically, an effective amount of the selective inhibitor of solTNF, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 2000 mg per kilogram body weight per day. An exemplary treatment regime entails administration once every day or once a week or once a month. A DN-TNF protein may be administered on multiple occasions. Intervals between single dosages can be daily, weekly, monthly or yearly. Alternatively, A DN-TNF protein may be administered as a sustained release formulation, in which case less frequent administration is required. Dosage and frequency vary depending on the half-life of the agent in the subject. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

Toxicity

Suitably, an effective amount (e.g., dose) of a DN-TNF protein described herein will provide therapeutic benefit without causing substantial toxicity to the subject. Toxicity of the agent described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in human. The dosage of the agent described herein lies suitably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: The Pharmacological Basis of Therapeutics, Ch. 1 (1975).

EXEMPLARY FEATURES AND EMBODIMENTS OF THE INVENTION

Certain preferred embodiments can be summarized as follows:

A method is disclosed for treating a subject suffering from chronic multisystem illness, specifically gulf war illness, the method comprising: administering to the subject a therapeutically effective amount of a selective inhibitor of solTNF, whereby the subject is treated; for purposes herein, this shall constitute "the method".

The selective inhibitor of solTNF may comprise a DN-TNF protein variant or a nucleic acid encoding the DN-TNF protein variant.

The DN-TNF protein variant may comprise XPro1595. Thus, in an embodiment, the method may comprise administering XPro1595 in a dose between 0.1 mg/kg and 10.0 mg/kg.

The DN-TNF protein can be administered: intravenously; subcutaneously; orally; via aerosol; via topical application; or via gene therapy. The gene therapy may comprise mesenchymal stem cells expressing a construct of the DN-TNF protein. The DN-TNF protein can be administered via gene modified autologous or allogeneic cellular therapy.

EXAMPLES

Example 1: Rat Model of GWI

As shown in FIG. 3, GWI was induced in rats by introducing di-isopropyl fluorophosphate (DFP) and waiting six months. In month seven, a selective inhibitor of solTNF known as XPro1595 (a.k.a. pegipanermin; 10 mg/kg), or PBS, was administered to the rats. MRI and behavioral testing were performed two weeks post treatment, including: depression by sucrose intake test; neuropathic pain analysis by hind paw mechanical hypersensitivity test; anxiety by marble burying test, open field test and elevated plus maze test; cognition by Barnes maze and novel object recognition test; memory by Morris water maze test. Other data observed includes: hippocampal (dentate gyrus) GFAP expression, IBA-1 expression, and hippocampal (CA1) spine density and morphology (Golgi staining). Animals were then euthanized for studies.

Figure 4:
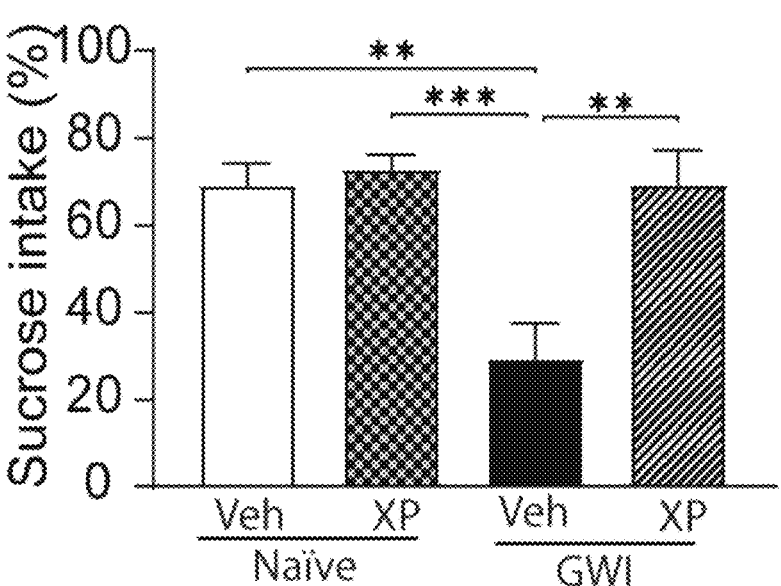
FIG. 4 shows results of a sucrose intake test for various experimental groups.

To test depression in the rats, a sucrose intake test was performed. Four groups were assessed, including naïve, naïve+XPro, GWI, and GWI+XPro. The data in FIG. 4 shows the GWI-induced rats exhibited a significant reduction in sucrose intake compared to both naïve groups and the GWI+XPro treated group. This suggests two things, (i) the GWI model is validated as the GWI group exhibited a significant reduction in sucrose intake, and (ii) the GWI+XPro treated group normalized to compare similarly with the naïve groups. In this regard, XPro treatment seems to resolve depression in the rodent model.

Figure 5:
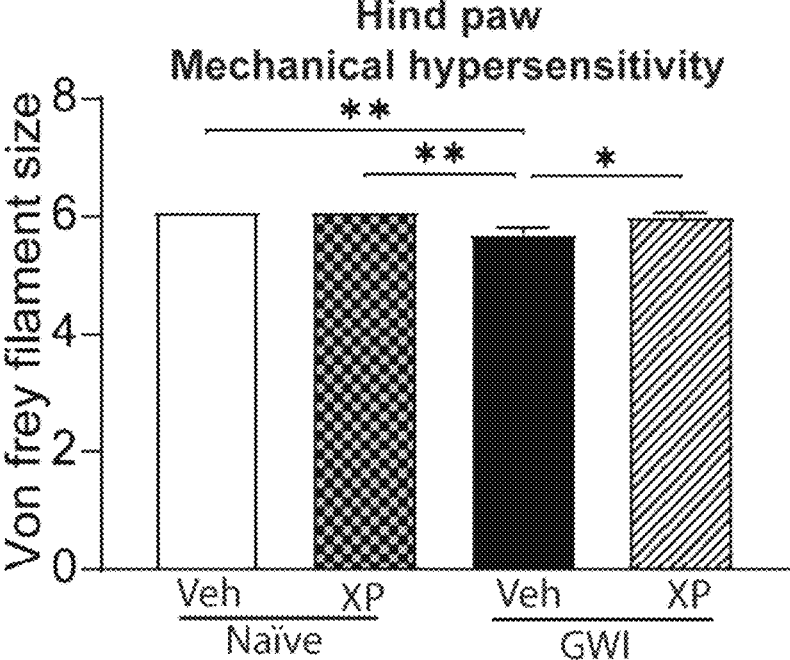
FIG. 5 shows results of a hind paw mechanical hypersensitivity test for the various experimental groups.

To test neuropathic pain, a hind paw mechanical hypersensitivity test was performed. The data represented in FIG. 5 shows that rats with DFP-induced GWI exhibited slightly more sensitivity to the Von Frey filament size.

Figure 6:
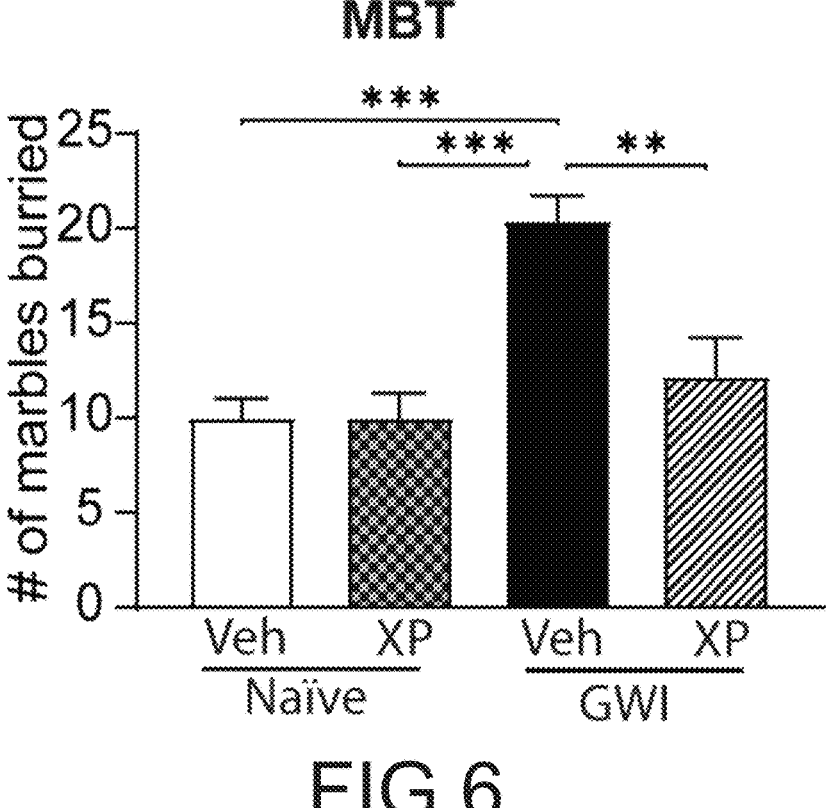
FIG. 6 shows results of a marble burying test for the various experimental groups.

To test anxiety, a marble burying test was performed. Surprisingly, as shown in FIG. 6, the DFP-induced GWI rats exhibited significantly more marbles buried compared to the naïve groups and the GWI+XPro treated group. This suggests the DFP-induced GWI rats demonstrated significantly more anxiety than the other groups, and the GWI+XPro treated group normalized to a state that is nearly identical to the naïve groups. In this regard, XPro treatment seems to resolve anxiety in the rodent model.

Figure 7:
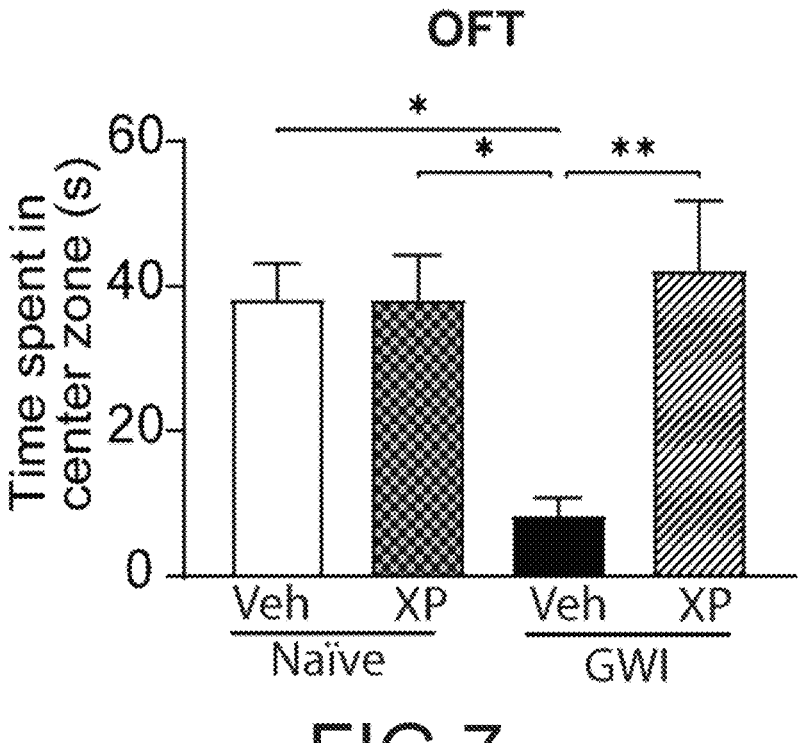
FIG. 7 shows results of an open field test for the various experimental groups.

In addition to marble burying, an open field test was administered to the various treated and control groups. As shown in FIG. 7, GWI rats exhibited substantially less time spent in center zones, whereas the GWI+XPro treated group exhibited activity very similar to naïve groups, indicating the XPro treatment resolved anxiety in the rats.

Moreover, an elevated plus maze was performed with the various treated and control groups. As shown in FIGS. 8-10, it was confirmed that GWI+XPro treated rats performed similar to naïve groups, whereas GWI rats underperformed. FIG. 8 shows percent of open arm entities in the various groups, whereas GWI rats comprised fewer open arm entities compared to naïve and treated groups. FIG. 9 shows percent of time spent in open arms of the maze for each experimental group, whereas GWI rats spend less time in open arms of the maze compared to naïve and treated groups. FIG. 10 shows an anxiety index for each of the experimental groups, whereas GWI rats exhibited greater anxiety compared to naïve and treated groups.

Barnes maze and novel object recognition tests were completed to assess cognition of the various groups in the study.

Figures 11A, 11B:
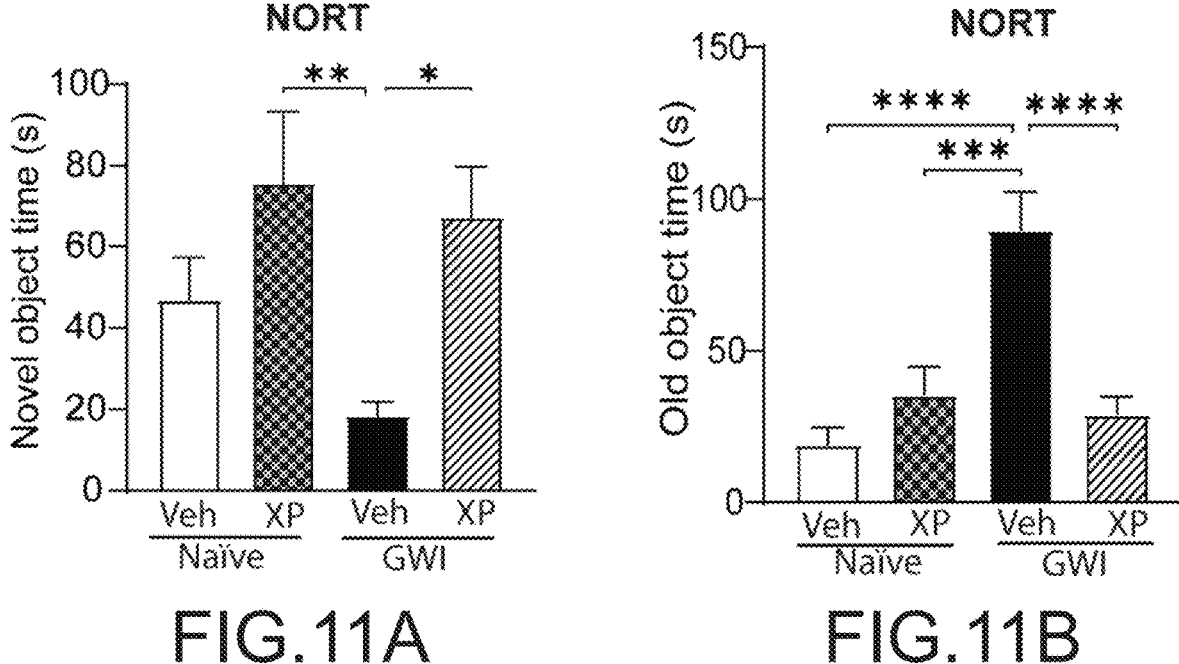
FIGS. 11(A-C) shows results of a novel object recognition test for the various experimental groups.
Figure 11C:
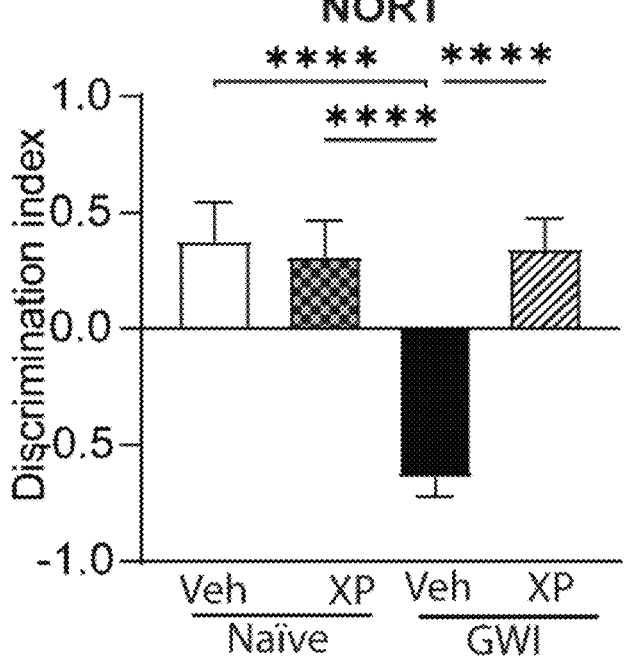
Figure 12A:
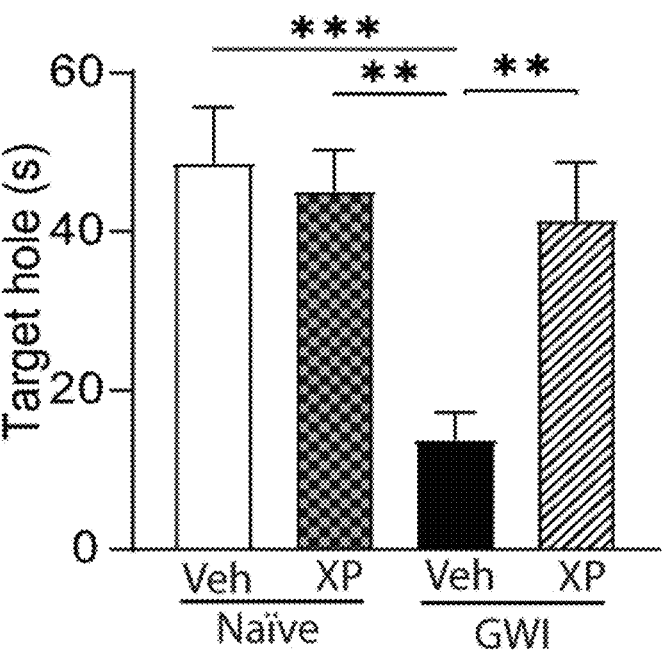
FIGS. 12(A-B) shows results of a Barnes maze cognition test for the various experimental groups.
Figure 12B:
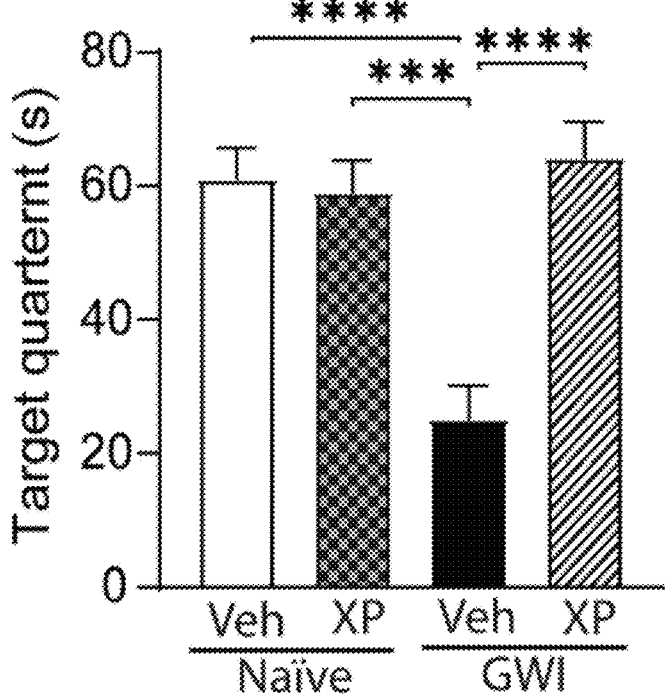

As shown in FIG. 11A, GWI rats spent less time with novel objects compared to naïve groups and the GWI+XPro treated group. FIG. 11B shows GWI rats spent more time with old objects compared to naïve groups and the GWI+ XPro treated group. GWI rats also exhibited a negative (−0.5) discrimination index as shown in FIG. 11C, whereas the naïve groups and the GWI+XPro treated group exhibited a positive up to 0.5 discrimination index, respectively. As shown in FIG. 12A, GWI rats spent less time in the target holes compared to naïve groups and the GWI+XPro treated group. FIG. 12B shows GWI rats spent less time in the target quadrant compared to naïve groups and the GWI+XPro treated group. These results indicate XPro treated rodents exhibit similar cognition to naïve groups, whereas the untreated GWI group underperformed comparatively.

Figure 13:
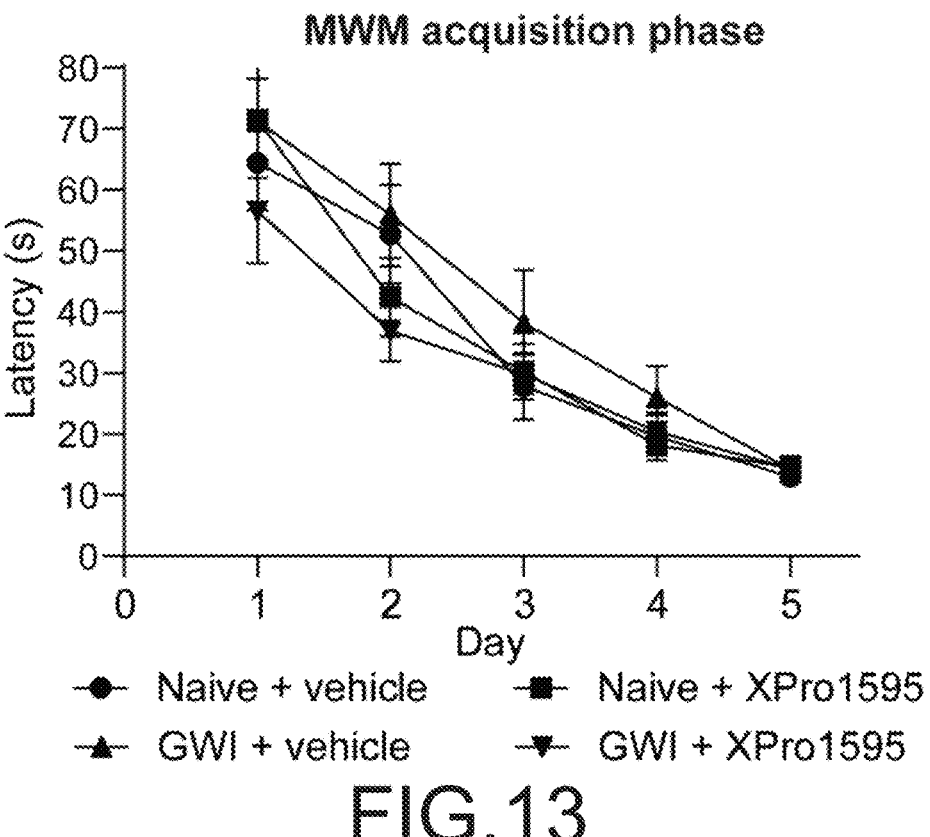
FIG. 13 shows the escape latency observed for each experimental group over a period of five days according to a Morris water maze test.
Figure 14:
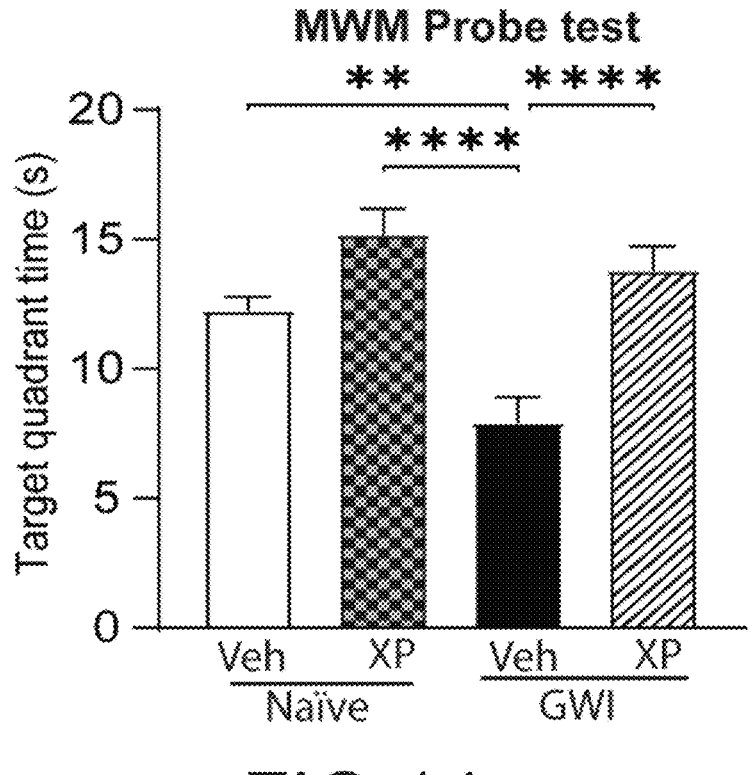
FIG. 14 shows target quadrant time for each of the experimental groups according to a Morris water maze test.

Next, a memory test was administered, the Morris Water Maze test. Again, the GWI+XPro treated group performed similar to naïve groups, whereas the GWI group underperformed comparatively. FIG. 13 shows the escape latency observed for each experimental group over a period of five days. FIG. 14 shows target quadrant time for each of the experimental groups. These data suggest memory capability is restored to a normal or near-normal level in XPro-treated rats.

Figure 15A:
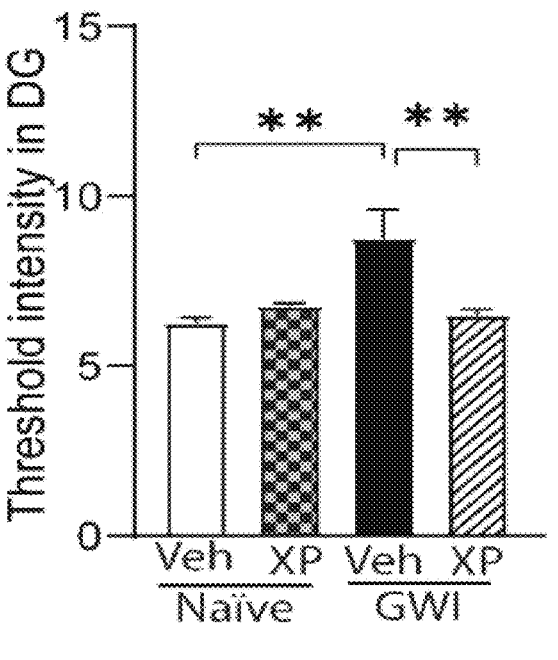
FIGS. 15(A-B) show results directed to GFAP (cells/ mm2) and percent of GFAP intensity for the various experimental groups in hippocampal dentate gyrus.
Figure 15B:
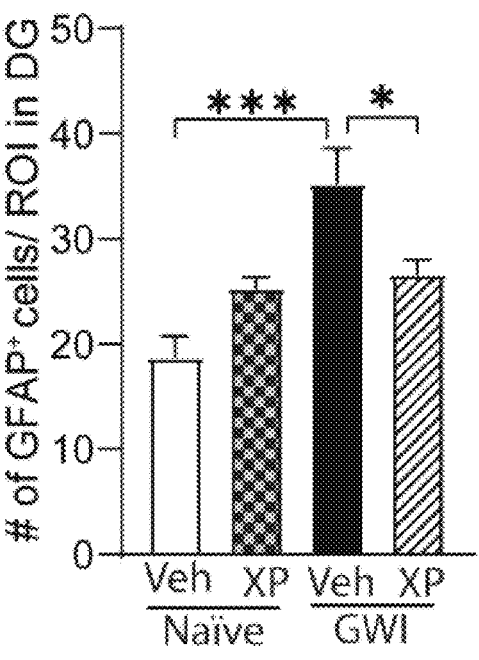

Hippocampal (Dentate Gyrus) GFAP expression was observed. As shown in FIGS. 15A-15B, respectively, the untreated GWI rats exhibited increased GFAP (cells/mm2) and percent of GFAP intensity, whereas the XPro-treated group was similar to naïve rats.

Figure 16A:
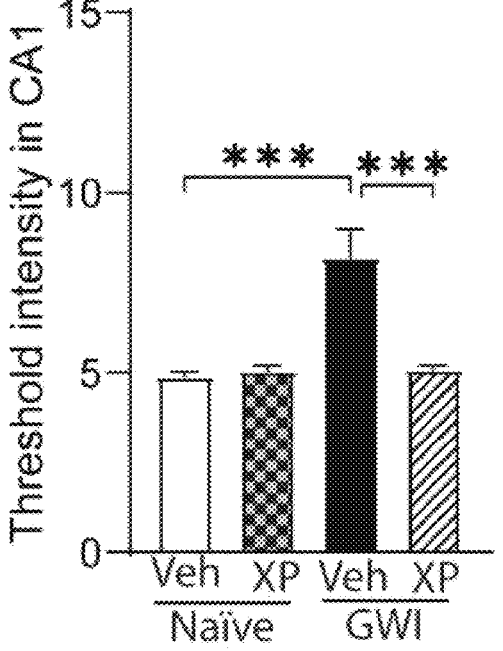
FIGS. 16(A-B) show results directed to GFAP (cells/ mm2) and percent of GFAP intensity for the various experimental groups in hippocampal CA1.
Figure 16B:
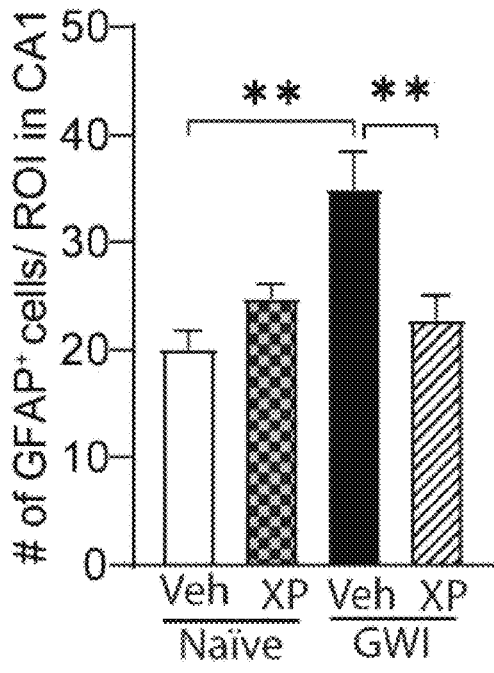

Hippocampal (CA1) GFAP expression was also observed. As shown in FIGS. 16A-16B, respectively, the untreated GWI rats exhibited increased GFAP (cells/mm2) and percent of GFAP intensity, whereas the XPro-treated group was similar to naïve rats.

Figure 17A:
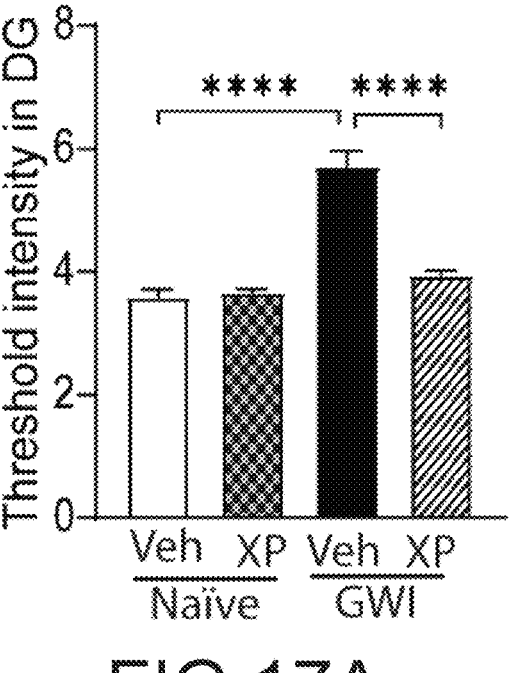
FIGS. 17(A-B) show results directed to IBA-1+(cells/ mm2) and percent of GFAP intensity for the various experimental groups in hippocampal dentate gyrus.
Figure 17B:
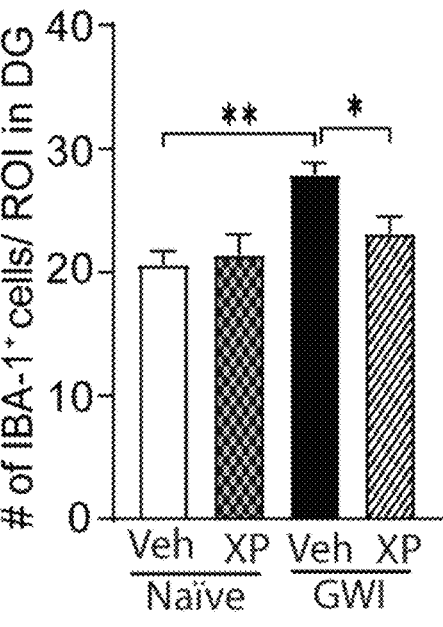

Hippocampal (Dentate Gyrus) IBA-1 expression was observed. As shown in FIGS. 17A-17B, respectively, the untreated GWI rats exhibited increased IBA-1 (cells/mm2) and percent of IBA-1 intensity, whereas the XPro-treated group was similar to naïve rats.

Figure 18A:
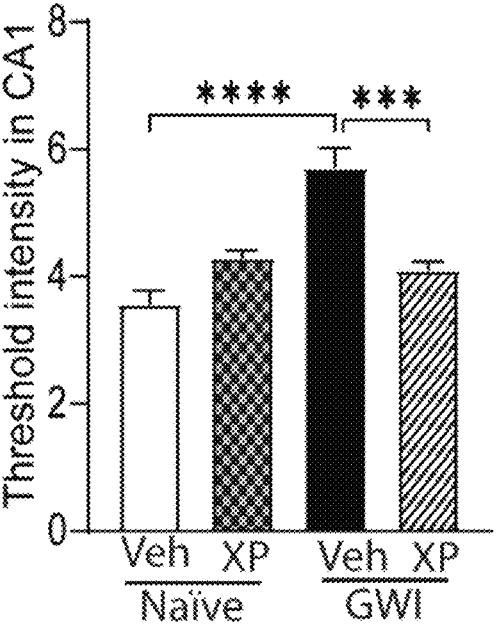
FIGS. 18(A-B) show results directed to IBA-1+(cells/ mm2) and percent of GFAP intensity for the various experimental groups in hippocampal CA1.
Figure 18B:
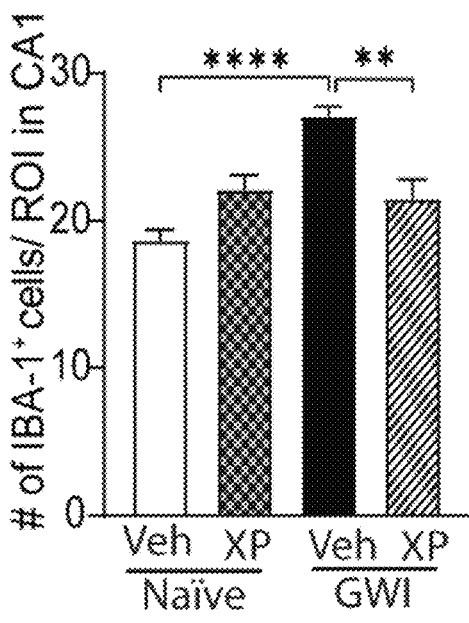

Hippocampal (CA1) IBA-1 expression was observed. As shown in FIGS. 18A-18B, respectively, the untreated GWI rats exhibited increased IBA-1 (cells/mm2) and percent of IBA-1 intensity, whereas the XPro-treated group was similar to naïve rats.

Figures 19A, 19B, 19C, 19D, 19E, 19F, 19G:
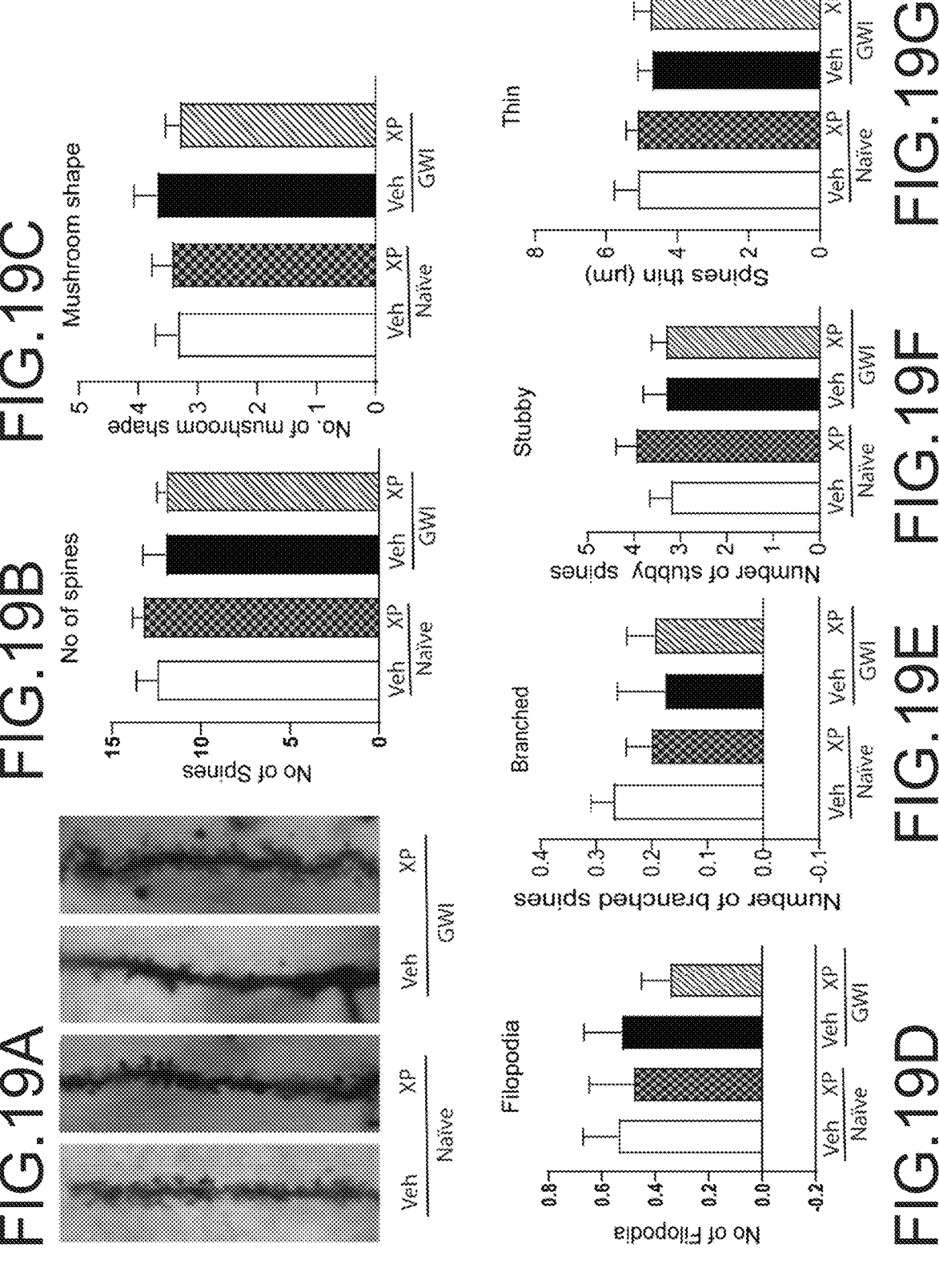
FIGS. 19(A-G) show hippocampal (CA1) spine density and morphology as observed for each experimental group, including number of spines, mushroom shape, filopodia, branched, stubby, and thin morphology, respectively.

Hippocampal (CA1) spine density and morphology was observed for each experimental group as shown in FIG. 19. FIG. 19A is an image showing morphology for the various experimental groups. FIG. 19B shows number of spines by experimental group. FIG. 19C shows number of mushroom shape morphology by experimental group. FIG. 19D shows number of filopodia by experimental group. FIG. 19E shows number of branched morphology by experimental group. FIG. 19F shows number of stubby morphology by experimental group. FIG. 19G shows number of thin morphology by experimental group.

Figures 20A, 20B, 20C:
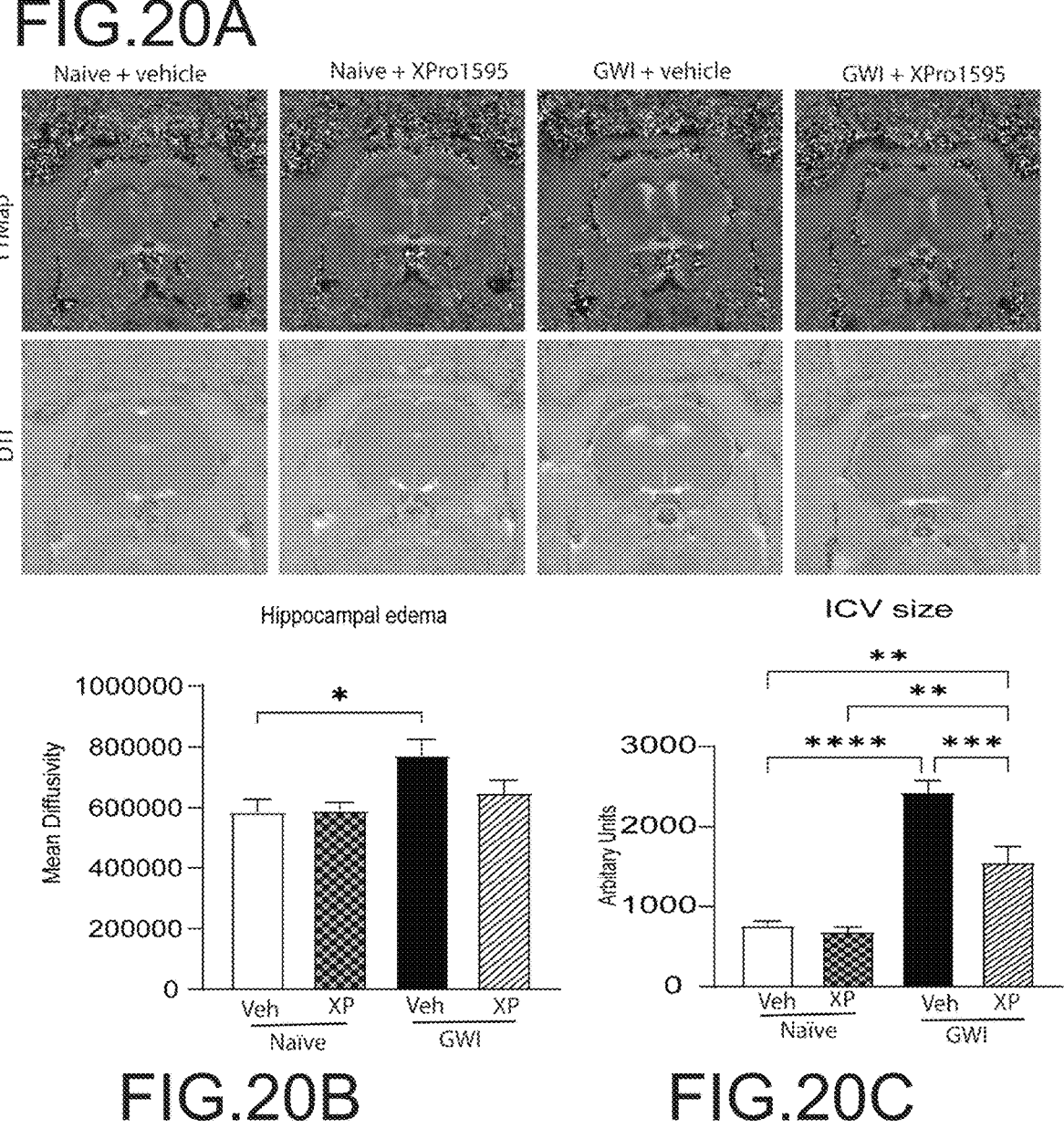
FIGS. 20(A-C) show MRI images for rats from each of a plurality of experimental groups, hippocampal edema, and intracranial volume (ICV size).

Moreover, magnetic resonance imaging was obtained for various experimental groups as shown in FIG. 20A. FIG. 20B shows hippocampal edema by experimental group. FIG. 20C shows intracranial volume (ICV size) for each experimental group. As shown, the GWI group exhibited increased edema and ICV size compared to control and XPro treated groups.

The data suggests that GWI may be treatable by selective solTNF inhibition, for example, using pegipanermin (XPro1595).

While the experimental data is based on treatment with XPro1595, a DN-TNF protein variant, it should be appreciated by one with skill in the art that other DN-TNF protein variants as described herein, or other selective inhibitors of solTNF, may be similarly implemented.

It is therefore proposed a method of treating Gulf War Illness in a subject in need thereof, comprising: administering to the subject a therapeutically effective amount of a selective inhibitor of solTNF that does not inhibit tmTNF signaling, whereby the subject is treated.

The selective inhibitor of solTNF may comprise XPro1595 (a.k.a. pegipanermin).

The therapeutically effective amount may preferably comprise between 0.1 mg/kg and 10.0 mg/kg.

CONCLUSION

The data suggests that GWI may be treatable by selective solTNF inhibition, for example, using pegipanermin (XPro1595) for selective solTNF blockade.

INDUSTRIAL APPLICABILITY

The invention finds utility in the treatment of MCI, and specifically GWI, and is therefore applicable to the medical field.

---

The invention claimed is:

1. A method of treating gulf war illness in a subject, comprising:

administering to the subject in need thereof a therapeutically effective amount of a dominant negative tumor necrosis factor (DN-TNF) protein variant, the DN-TNF protein variant comprising the amino acid sequence of wild-type tumor necrosis factor according to SEQ ID NO. 3 modified with one to seven amino acid substitutions, wherein the substitutions are each selected from the group consisting of: V1M, Q21C, Q21R, E23C, N30D, R31C, R31I, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, C101A, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R, whereby the subject is treated.

2. The method of claim 1, wherein the DN-TNF protein variant further comprises up to twenty amino acid insertions or deletions.

3. The method of claim 2, wherein the DN-TNF protein variant comprises pegipanermin.

4. The method of claim 3, wherein the method comprises administering pegipanermin in a dose between 0.1 mg/kg and 10.0 mg/kg.

5. The method of claim 2, wherein the DN-TNF protein variant is administered: intravenously; subcutaneously; orally; via aerosol; via topical application; or via gene therapy.

6. The method of claim 5, wherein the gene therapy comprises mesenchymal stem cells expressing a construct of the DN-TNF protein variant.

7. The method of claim 1, wherein the DN-TNF variant protein comprises the amino acid sequence of SEQ ID NO. 3 modified with the amino acid substitutions V1M, R31C, C69V, Y87H, C101A, and A145R.

8. The method of claim 1, wherein the DN-TNF variant protein comprises the amino acid sequence of SEQ ID NO. 3 modified with at least the amino acid substitutions I97T, and A145R.

* * * * *

SEQUENCE LISTING

```
Sequence total quantity: 3
SEQ ID NO: 1              moltype = DNA  length = 495
FEATURE                   Location/Qualifiers
source                    1..495
                          mol_type = unassigned DNA
                          organism = Homo sapiens
SEQUENCE: 1
atgcaccacc accaccacca cgtacgctcc tcctcccgca ctccgtccga caaaccggta  60
gctcacgtag tagctaaccc gcaggctgaa ggtcagctgc agtggctgaa ccgccgcgct  120
aacgctctgc tggctaacgg tgtagaactg cgcgacaacc agctggtagt accgtccgaa  180
ggtctgtacc tgatctactc ccaggtactg ttcaaaggtc agggttgtcc gtccactcac  240
gtactgctga ctcacactat ctcccgcatc gctgtatcct accagactaa agtaaacctg  300
ctgtccgcta tcaaatcccc gtgtcagcgc gaaactccgg aaggtgctga agctaaaccg  360
tggtacgaac cgatctacct gggtggtgta ttccagctgg aaaaaggtga ccgcctgtcc  420
gctgaaatca accgcccgga ctacctggac ttcgctgaat ccggtcaggt atacttcggt  480
atcatcgctc tgtga                                                   495

SEQ ID NO: 2              moltype = AA  length = 164
FEATURE                   Location/Qualifiers
source                    1..164
                          mol_type = protein
                          organism = Homo sapiens
SEQUENCE: 2
MHHHHHHVRS SSRTPSDKPV AHVVANPQAE GQLQWLNRRA NALLANGVEL RDNQLVVPSE  60
GLYLILSQVL FKGQGCPSTH VLLTHTISRI AVSYQTKVNL LSAIKSPCQR ETPEGAEAKP  120
WYEPIYLGGV FQLEKGDRLS AEINRPDYLD FAESGQVYFG IIAL                   164

SEQ ID NO: 3              moltype = AA  length = 157
FEATURE                   Location/Qualifiers
source                    1..157
                          mol_type = protein
                          organism = Homo sapiens
SEQUENCE: 3
VRSSSRTPSD KPVAHVVANP QAEGQLQWLN RRANALLANG VELRDNQLVV PSEGLYLIYS  60
QVLFKGQGCP STHVLLTHTI SRIAVSYQTK VNLLSAIKSP CQRETPEGAE AKPWYEPITL  120
GGVFQLEKGD RLSAEINRPD YLDFAESGQV YFGIIAL                          157
```